(12) United States Patent
Donaldson (10) Patent No.: US 10,150,282 B2
(45) Date of Patent: Dec. 11, 2018

(54) SYSTEM AND METHOD FOR ADDITIVE MANUFACTURE OF CHEMICAL DELIVERY DEVICES USING HALFTONE SCREENING

(71) Applicant: Xerox Corporation, Norwalk, CT (US)

(72) Inventor: Patricia J. Donaldson, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 188 days.

(21) Appl. No.: 15/294,676

(22) Filed: Oct. 14, 2016

(65) Prior Publication Data

US 2018/0104911 A1 Apr. 19, 2018

(51) Int. Cl.
| | |
|---|---|
| *B33Y 50/02* | (2015.01) |
| *B33Y 30/00* | (2015.01) |
| *H04N 1/405* | (2006.01) |
| *A61J 3/07* | (2006.01) |
| *A61J 3/10* | (2006.01) |
| *A61K 9/20* | (2006.01) |
| *B29C 64/112* | (2017.01) |

(Continued)

(52) U.S. Cl.
CPC .............. *B33Y 50/02* (2014.12); *A61J 3/07* (2013.01); *A61J 3/10* (2013.01); *A61K 9/2095* (2013.01); *B29C 64/112* (2017.08); *B29C 64/393* (2017.08); *B29C 67/0059* (2013.01); *B29C 67/0088* (2013.01); *B29C 67/0092* (2013.01); *B33Y 10/00* (2014.12); *B33Y 30/00* (2014.12); *B33Y 80/00* (2014.12); *H04N 1/405* (2013.01); *B29C 64/165* (2017.08)

(58) Field of Classification Search
CPC ......... B33Y 50/00; B33Y 50/02; B33Y 10/00; B33Y 30/00; B33Y 80/00; B29C 64/112; B29C 64/165; B29C 64/386; B29C 64/393; H04N 1/405–1/4058; H04N 1/52; A61J 3/07; A61J 3/10; A61K 9/2095
See application file for complete search history.

(56) References Cited

U.S. PATENT DOCUMENTS

| | | | |
|---|---|---|---|
| 6,280,771 | B1 | 8/2001 | Monkhouse et al. |
| 6,375,874 | B1 | 4/2002 | Russell et al. |

(Continued)

FOREIGN PATENT DOCUMENTS

EP    1 264 679 A2    12/2002

OTHER PUBLICATIONS

Oh et al.; Hydrodynamic micro-encapsulation of aqueous fluids and cells via 'on the fly' photopolymerization; Journal of Micromechanics and Microengineering; Jan. 9, 2006; pp. 285-291; vol. 16; Institute of Physics Publishing Ltd., UK.

(Continued)

*Primary Examiner* — Scott A Rogers
(74) *Attorney, Agent, or Firm* — Maginot Moore & Beck LLP (57) ABSTRACT

A method of forming a chemical delivery device with an active chemical includes generating halftoned image data using a stochastic halftone screen and with reference to a concentration parameter for the active chemical. The method also includes ejecting a chemical carrier including the active chemical into a portion of a plurality of cavities formed in the chemical delivery device based on the halftoned image data to produce the chemical delivery device with a concentration of the active chemical corresponding to the concentration parameter.

10 Claims, 5 Drawing Sheets

(51) Int. Cl.
    *B29C 64/393*      (2017.01)
    *B33Y 10/00*      (2015.01)
    *B33Y 80/00*      (2015.01)
    *B29C 67/00*      (2017.01)
    *B29C 64/165*      (2017.01)

(56) References Cited

U.S. PATENT DOCUMENTS

| | | | |
|---|---|---|---|
| 6,454,811 B1 | 9/2002 | Sherwood et al. | |
| 9,286,554 B1 | 3/2016 | Maltz et al. | |
| 9,787,871 B2 * | 10/2017 | Schweid | G06F 17/50 |
| 9,955,041 B2 * | 4/2018 | Schweid | G06K 15/102 |
| 2002/0079601 A1 | 6/2002 | Russell et al. | |
| 2003/0099708 A1 | 5/2003 | Rowe et al. | |
| 2005/0233000 A1 | 10/2005 | Figueroa et al. | |
| 2010/0007692 A1 | 1/2010 | Vanmaele et al. | |
| 2011/0285054 A1 | 11/2011 | Eliahu | |
| 2012/0315333 A1 | 12/2012 | Zhou et al. | |
| 2013/0193621 A1 | 8/2013 | Daya et al. | |
| 2014/0134320 A1 | 5/2014 | Chang et al. | |
| 2014/0277661 A1 | 9/2014 | Amadio et al. | |
| 2015/0165020 A1 | 6/2015 | Jaklenec et al. | |
| 2015/0201500 A1 | 7/2015 | Shinar et al. | |
| 2015/0320158 A1 | 11/2015 | Duffy, Jr. et al. | |
| 2017/0246811 A1 * | 8/2017 | Donovan | B29C 67/0088 |
| 2018/0052447 A1 * | 2/2018 | Morovic | H04N 1/405 |

OTHER PUBLICATIONS

Carmen Drahl; These Wax Capsules Might Make Chemists Lives Easier; Forbes.com LLC; Aug. 12, 2015; 3 Pages; http://onforb.es/1gAeZwM.

Biancamaria Baroli; Photopolymerization of Biomaterials: issues and potentialities in drug delivery, tissue engineering, and cell encapsulation application; Journal of Chemical Technology and Biotechnology; 2006; pp. 491-499.

European Search Report related to Application No./Patent No. 17 19 27452-1019 dated Mar. 15, 2018; 6 Pages.

* cited by examiner

SYSTEM AND METHOD FOR ADDITIVE MANUFACTURE OF CHEMICAL DELIVERY DEVICES USING HALFTONE SCREENING

TECHNICAL FIELD

This disclosure is directed to systems and methods of additive manufacture and, more particularly, to systems and methods for manufacturing tablets or other items with substrates that provide controlled release of a chemical using three-dimensional object printers.

BACKGROUND

Three-dimensional printing, also known as additive manufacturing, is a process of making a three-dimensional solid object from a digital model of virtually any shape. Many three-dimensional printing technologies use an additive process in which an additive manufacturing device forms successive layers of the part on top of previously deposited layers. Some of these technologies use inkjet printing, where one or more printheads eject successive layers of material. Three-dimensional printing is distinguishable from traditional object-forming techniques, which mostly rely on the removal of material from a work piece by a subtractive process, such as cutting or drilling.

Additive manufacturing systems can produce a wide range of items with some proposed uses including encapsulation of chemicals in soluble substrates for the delivery of medications or more broadly to chemical delivery devices. The additive manufacturing system deposits an "active chemical" in the chemical delivery device that is suspended in an excipient material of a substrate that dissolves in a solvent. As used herein, the term "active chemical" refers to any chemical that is embedded within a chemical delivery device for controlled release over time as the chemical delivery device dissolves in a solvent. As used herein, the term "excipient material" refers to one or more types of material that form a structure of a chemical delivery device, encapsulate one or more active chemicals, and control the release of the active chemicals within the chemical delivery device as the chemical delivery device dissolves in a solvent or melts in a temperature-controlled chemical release process. In many embodiments, the excipient materials are substantially non-reactive with the active chemical, but the excipient materials are soluble in some form of solvent that dissolves the chemical delivery device to emit the active chemical during use of the chemical delivery device. Excipient substrate materials are known to the art that dissolve in various solvents including water, acids, bases, polar and non-polar solvents, or any other suitable solvent for different applications. Corn starch and microcrystalline cellulose are two examples of materials that are commonly used as excipient materials for an active chemical ingredient, although other materials include gelatins, polymers, including UV-curable polymers, and the like that are used in various chemical delivery devices. Some forms of excipient material dissolve to deliver the active chemical by melting or otherwise disintegrating at an operating temperature, such as an elevated melting temperature that is higher than the typical ambient storage temperature for the chemical delivery device.

As the substrate dissolves, the active chemical releases into a medium around the chemical delivery device and produces a chemical reaction. Applications for such devices include, but are not limited to, medicament delivery in human and veterinary medicine, fertilizer and pesticide delivery for agriculture and horticulture, dye release for tracking the flow of water or other fluids, and delivery of an active chemical in an industrial process.

While prior art additive manufacturing systems can produce chemical delivery devices, some forms of chemical delivery devices require additional structural elements for proper operation. For example, some time-release chemical delivery devices require a specific concentration gradient of an active chemical to deliver a dose of the active chemical that varies over time. In some instances, the tablet does not deliver the active chemical at a desired rate if the active chemical is distributed within the volume of the tablet in a non-uniform manner. For example, the rate of release from the tablet can be too high at some points during the dissolving of the tablet when it delivers a larger concentration of the active chemical than intended. Also, the rate of release can be too low when the tablet delivers too low of a concentration of the active chemical at particular point in time after it is digested. Additionally, some tablets include two or more types of active chemicals that should not mix while in the tablet, but should mix once the tablet dissolves. Consequently, improvements to additive manufacturing processes and systems that enable production of tablets with precise distributions of active chemicals would be beneficial.

SUMMARY

In one embodiment, a method of producing a chemical delivery device with a three-dimensional object printer has been developed. The method includes receiving with a controller a first concentration parameter for a first active chemical in a first region of a substrate in the chemical delivery device, generating with the controller halftoned image data using a stochastic halftone screen and with reference to the first concentration parameter, the halftoned image data including a plurality of activated pixels that correspond only to locations of a first portion of a plurality of cavities formed in a substrate that receive the first active chemical, and ejecting with at least a first ejector a predetermined amount of a first chemical carrier including the first active chemical into each cavity in the first portion of the cavities in the substrate with reference to the halftoned image data to produce the chemical delivery device with a concentration of the first active chemical corresponding to the first concentration parameter.

In another embodiment, a three-dimensional object printer that is configured to produce a chemical delivery device has been developed. The three-dimensional object printer includes a support member, at least a first ejector configured to eject a first chemical carrier including a first active chemical toward the support member, and a controller operatively connected to the at least first ejector and a memory. The controller is configured to receive a first concentration parameter for a first active chemical in a first region of a substrate in a chemical delivery device positioned on the support member, generate halftoned image data using a stochastic halftone screen stored in the memory and with reference to the first concentration parameter, the halftoned image data including a plurality of activated pixels that correspond only to locations of a first portion of a plurality of cavities formed in a substrate that receive the first active chemical, and operate the at least first ejector to eject a predetermined amount of a first chemical carrier including the first active chemical into each cavity in the first portion of the cavities in the substrate with reference to the halftoned image data to produce the chemical delivery device with a concentration of the first active chemical corresponding to the first concentration parameter.

BRIEF DESCRIPTION OF THE DRAWINGS

The foregoing aspects and other features of an additive manufacturing device or printer that produces chemical delivery devices including at least one active chemical are explained in the following description, taken in connection with the accompanying drawings.

DETAILED DESCRIPTION

For a general understanding of the environment for the device disclosed herein as well as the details for the device, reference is made to the drawings. In the drawings, like reference numerals designate like elements.

As used herein, the term "halftone screen" refers to a two-dimensional or three-dimensional arrangement of numeric threshold values that are used to control a distribution of materials to form a three-dimensional printed object, such as a chemical delivery device. Each entry in the halftone screen is referred to as a "dot" herein. The dots are arranged in either a two-dimensional space for a two-dimensional halftone screen or a three-dimensional space for three-dimensional halftone screen. The term "dot center" refers to a single dot that serves as a central location for a group of multiple dots that are each assigned a threshold value based on the value of the dot center. For example, in some embodiments a controller generates a particular threshold value at a dot center and "grows" a set of dots with the same threshold value around the dot center. In other configurations, a dot center corresponding to a cavity that is a candidate to receive an active chemical is surrounded by "guard" dots that have a fixed value corresponding to excipient material that encapsulates the cavity. The dot center corresponds to a location in the halftone screen and the final image data that optionally receives an active chemical, based on the concentration parameter of the active chemical and the value of the threshold in the dot center. The surrounding dots each correspond to locations that receive excipient material and do not receive an active material to ensure that the active material is encapsulated within the chemical delivery device.

As described in more detail below, a printer uses the halftone screens in conjunction with concentration parameter data for one or more active chemicals to generate "halftoned image data" or more simply "image data". The image data include two-dimensional or three-dimensional arrangements of locations that specify a type of material in the chemical delivery device with each location in the image data being referred to as a "pixel" herein. Each pixel in the image data corresponds to the location of one dot in a halftone screen. However, instead of the threshold values in the dots of the halftone screens, the pixels in the image data each include a value that specifies one type of excipient material or active material that the printer emits to form a chemical delivery device with concentration levels of the active chemical that correspond to the concentration parameters. The term pixel as used herein also includes the ordinary meaning of the term "voxel" (volumetric-pixel) that refers to the three-dimensional volumetric units that form the shape and structure of a model for a three-dimensional printed object. A three-dimensional object printer uses the image data to control the operation of ejectors or other material dispensers to form the structure and distribute the active chemicals in a chemical delivery device.

As used herein, the term "stochastic halftone screen" refers to a halftone screen in which dot centers are uniformly sized and pseudo-randomly distributed throughout a two or three dimensional space. Traditional, fixed frequency halftone screens establish a set of dot centers at fixed points, usually based on a crystalline lattice. Common halftone screens might place dot centers at the vertices of a square or hexagonal lattice in two dimensions (or at the vertices of cubes, or the centers of close-packed spheres in three dimensions). A fixed frequency halftone screen increases the number of dots which are "on" by adding additional dots next to an existing dot center. Stochastic screens increase the number of dots that correspond to a particular threshold value or range of threshold values by adding additional dot centers, which are generally not adjacent to a previous dot center.

As used herein, the term "vector halftone screen" refers to a type of halftone screen where a single halftone screen positions multiple types of active chemicals in different locations to prevent mixing of different active chemicals during the manufacturing process of a chemical delivery device. The vector halftone screen differs from many prior art halftone screens that are associated with printed images where each color in a multi-color printer (e.g. a cyan, magenta, yellow, black) printer has a separate halftone screen and the printer generates a separate set of image data for each color, which is often referred to as a "color separation". In conventional printing, many printed images include halftoned image data in multiple color separations that print two colors of ink to the same physical location on a sheet of paper as part of a printed image, which is sometimes desirable when printing color images. However, in many chemical delivery device embodiments, different active chemicals, which are analogous to different colors of ink, should not be printed in a single physical location since the active chemicals should only mix upon being released from the chemical delivery device. By contrast, the vector halftone screens enable forming chemical delivery devices that employ multiple active chemicals, using a single halftone screen that prevents multiple active chemicals from being printed to a single location.

Using the vector halftone screen, a controller assigns different threshold ranges to different active chemicals based on the concentration parameter value of each active chemical. The threshold ranges do not overlap so that each dot center within the vector halftone can be assigned to at most one type of active chemical or to an excipient material for dots that do not correspond to any active chemical. At each dot location in the halftone screen, a controller identifies the threshold value in the halftone screen and generates a pixel of image data that corresponds to at most one active chemical based on "stacked" threshold levels for one or more active chemicals. For halftone dots with threshold values that do not correspond to the ranges for any active chemicals, the controller generates an image data pixel corresponding to an excipient material that fills the pixel.

As is described in more detail below in conjunction with FIG. 5, one practical embodiment of the halftone screen includes dots with an 8-bit numeric range of threshold values (0-255). A controller receives concentration parameters, optionally as a percentage value, and assigns non-overlapping or "stacked" portions of the 8-bit numeric range to each concentration parameter based on the size of the concentration parameters (e.g. 25% for Chemical A→0-63; 16% for Chemical B→64-104; and Excipient material for the remaining values 105→255). The controller uses the dot values of the vector halftone screens at different locations to determine which compound is printed for each corresponding pixel in the image data by assigning each dot to one chemical based on the value of the dot and the numeric ranges of each chemical (e.g. a dot value of 24→image data pixel for Chemical A; a dot value of 134→image data pixel for Excipient material). The statistical distribution of threshold values within the vector halftone screen ensures that multiple chemicals are distributed evenly within each region of the chemical delivery device. Thus, the vector halftone screen and corresponding halftone process enables generation of image data that correspond to a distribution of one or more active chemicals that prevents mixing of the active chemicals during the process of producing the chemical delivery device.

The terms "stochastic halftone screen" and "vector halftone screen" as used herein do not refer to mutually exclusive properties of halftone screens. Instead, a single halftone screen can have both the stochastic and vector properties described above that form a stochastic vector halftone screen. For example, in a chemical delivery device that only uses a single active chemical, a stochastic halftone screen enables production of the chemical delivery device with a distribution of the single active chemical in different regions of the chemical delivery device based on concentration parameters for the single active chemical in each of the regions. While the halftone screen in the single chemical configuration is optionally a vector halftone screen, the vector property is not required since there is only a single active chemical. In production of chemical delivery devices that include two or more active chemicals, the printer utilizes a halftone process with the stochastic vector halftone screen to control the distribution of two or more active chemicals within the chemical delivery device.

As used herein, the term "process direction" refers to a direction of movement of a support member past one or more printheads during a three-dimensional object formation process. The support member holds the three-dimensional object during the print process. In some embodiments, the support member is a planar member such as a metal plate, while in other embodiments the support member is a rotating cylindrical member or a member with another shape that supports the formation of an object during the three-dimensional object printing process. In some embodiments, the printheads remain stationary while the support member and object moves past the printhead. In other embodiments, the printheads move while the support member remains stationary. In still other embodiments, both the printheads and the support member move.

As used herein, the term "cross-process direction" refers to a direction that is perpendicular to the process direction and in the plane of the support member. The ejectors in two or more printheads are registered in the cross-process direction to enable an array of printheads to form printed patterns of an excipient material or active chemical material over a two-dimensional planar region. During a three-dimensional object printing process, the printheads eject drops of the excipient material to form successive layers of structure and cavities within a chemical delivery device.

As used herein, the term "z-axis" refers to an axis that is perpendicular to the process direction, the cross-process direction, and to the plane of the support member in a three-dimensional object printer. At the beginning of the three-dimensional object printing process, a separation along the z-axis refers to a distance of separation between the support member and the printheads that form the layers of excipient material in a three-dimensional printed chemical delivery device. As the ejectors in the printheads form each layer of excipient material, the printer adjusts the z-axis separation between the printheads and the uppermost layer to maintain a substantially constant distance between the printheads and the uppermost layer of the object during the printing operation. In some embodiments, the support member moves away from the printheads during the printing operation to maintain the z-axis separation, while in other embodiments the printheads move away from the partially printed object and support member to maintain the z-axis separation.

Figure 1:
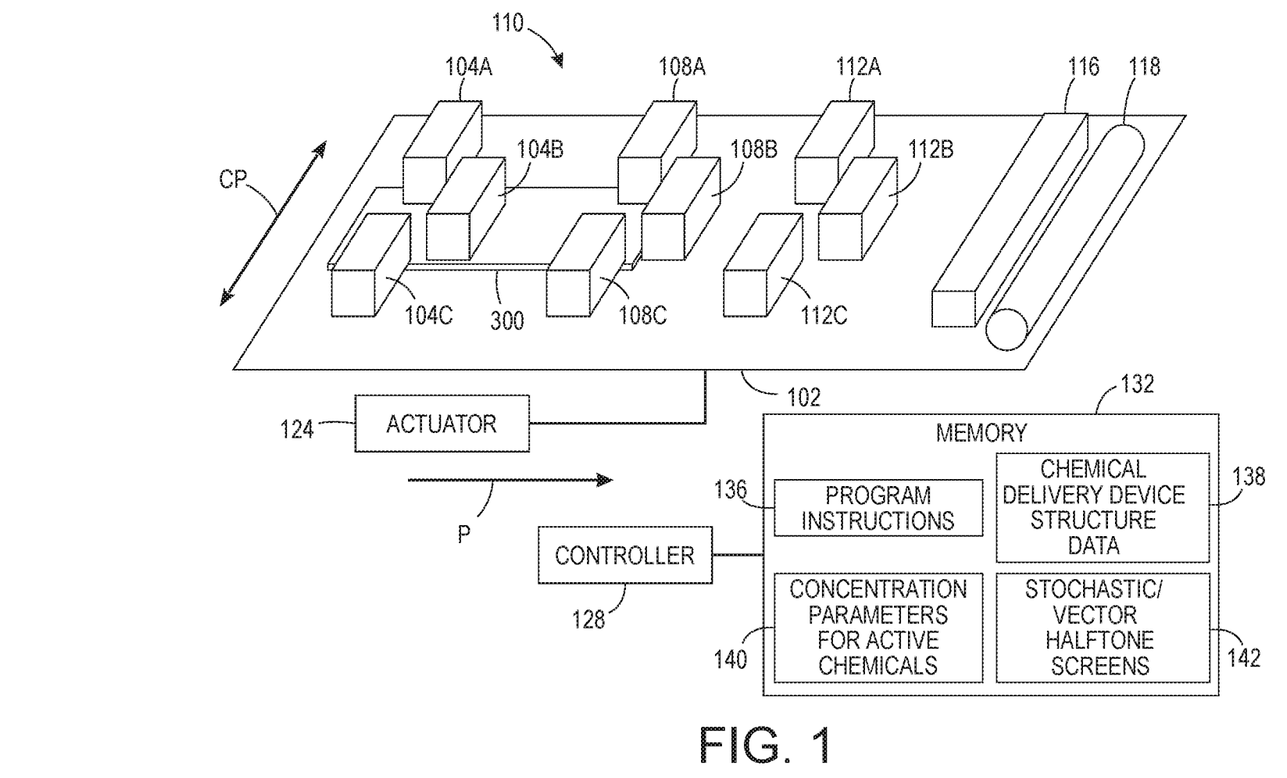
FIG. 1 is a diagram of a three-dimensional object printer that is configured to form chemical delivery devices.

FIG. 1 depicts an additive manufacturing device embodied as a three-dimensional object printer 100, or more simply printer 100. The printer 100 is configured to operate printheads to form a three-dimensional printed chemical delivery device 300 that includes one or more active chemicals encapsulated within a structure formed from at least one type of excipient material. The printer 100 includes a support member 102, printhead arrays 104A-104C, 108A-108C, and 112A-112C, an ultraviolet (UV) curing device 116, controller 128, memory 132, and a leveler 118. In the illustrative embodiment of FIG. 1, the three-dimensional object printer 100 is depicted during formation of a three-dimensional chemical delivery device 300 that is formed from a plurality of layers of excipient material. The chemical device 300 includes multiple layers of cavities that receive active chemicals in the form of drops of chemical carriers that one or more ejectors in the printhead arrays 104A-104C and 108A-108C eject into portions of the cavities with reference to concentration parameters in different regions of the chemical delivery device 300.

In the embodiment of FIG. 1, the support member 102 is a planar member, such as a metal plate, that moves in a process direction P. The printhead arrays 104A-104C, 108A-108C, and 112A-112C, UV curing device 116, and leveler 118 form a print zone 110. The member 102 carries any previously formed layers of excipient material along with cavities that have been filled with an active chemical material through the print zone 110 in the process direction P. During the printing operation, the support member 102 moves in a predetermined process direction path that passes the printheads multiple times to form successive layers of the excipient material and active chemicals in the chemical delivery device 300. In some embodiments, multiple members similar to the member 102 pass the print zone 110 in a carousel or similar configuration. One or more actuators move the member 102 through the print zone 110 in the process direction P. In the embodiment of FIG. 1, an actuator also moves the support member 102 in the direction Z away from the components in the print zone 110 after each layer of excipient material is applied to the support member 102 to form the chemical delivery device 300. The actuator moves the support member 102 in the Z direction to maintain a uniform separation between the uppermost layer of the chemical delivery device 300 and the components in the print zone 110.

Each of the printheads in the printhead arrays 104A-104C, 108A-108C, and 112A-112C includes at least one ejector. In the illustrative printhead embodiments of FIG. 1, each printhead includes a two-dimensional array of ejectors that eject drops of liquid using, for example, piezoelectric or thermal transducers. In many practical embodiments, each printhead includes an ejector array with a density that enables printing of several hundred or thousand drops of material per linear inch (DPI). The printer 100 depicted in FIG. 1 ejects drops of two different types of active chemical with the printhead array 104A-104C being configured to eject drops of a first active chemical and the printhead array 108A-108C being configured to eject drops of the second active chemical. The printhead array 112A-112C ejects drops of an excipient material, such as a polymer material, which forms the structure of the chemical delivery device 300, including the cavities within the chemical delivery device 300 that receive active chemicals.

In many embodiments, the active chemical is dissolved or suspended in a chemical carrier for ejection as liquid drops through the inkjets in the printheads 104A-104C and 108A-108C. In some configurations, the chemical carrier evaporates within the cavities of the chemical delivery device 300 prior to sealing each cavity to leave the active chemical in the cavity, while in other embodiments the chemical carrier remains in a liquid state within the cavity. While the precise formulation of the chemical carrier can vary for different types of chemical delivery devices, the chemical carrier is generally a liquid form of an excipient material. That is to say, the chemical carrier does not interact with the active chemicals or substantially change the nature of the chemical reaction as the chemical delivery device dissolves and emits the active chemicals. Of course, some active chemicals are already available in a liquid form that is compatible with the printheads and ejectors in the printer 100. In these configurations, the chemical carrier and the active chemical are the same material.

While each of the printhead arrays 104A-104C, 108A-108C, and 112A-112C is depicted as including three printheads, alternative configurations can include fewer printheads or a greater number of printheads to accommodate print zones with different sizes in the cross-process direction. Alternative embodiments of the printer 100 include a greater or lesser number of printhead arrays to handle different combinations of active chemicals. While the printhead arrays 104A-104C, 108A-108C, and 112A-112C remain stationary during operation in the printer 100, alternative printer embodiments include one or more printheads that move in the cross-process direction CP, process direction P, or in both the cross-process and process directions. The moving printheads form the structure of a three-dimensional chemical delivery device and deposit active chemicals within the chemical delivery device. Additionally, while FIG. 1 depicts a single chemical delivery device 300 for illustrative purposes, in many practical embodiments the printer 100 forms multiple chemical delivery devices simultaneously, such as a sheet of the excipient material containing multiple tablets that can be swallowed by an average human, using the printhead arrays depicted in FIG. 1. The larger excipient material sheet is then mechanically separated into individual chemical delivery devices after completion of the operation of the printer 100.

In the embodiment of the printer 100 shown in FIG. 1, the printheads 112A-112C act as a dispenser for the excipient material. In an alternative configuration to the print zone 110, an excipient powder dispenser includes a spreader (not shown) that emits the excipient material as a thin layer of powder that covers the upper surface of the chemical delivery device 300. The powder dispenser is positioned across the print zone 110 in a similar configuration to the UV curing device 116. The ejectors in the printheads 112A-112C eject drops of a liquid binder material onto selected locations of each powder layer to bind and harden the powder into a durable portion of the chemical delivery device. The UV curing device 116 optionally cures the binder in some embodiments. The excess powder that does not receive the binder is removed from the chemical delivery device 300 to expose cavities that receive the chemical carrier that includes the active chemicals from the printhead arrays 104A-104C and 108A-108C.

In the printer 100, the UV curing device 116 is an ultraviolet light source that produces UV light across the print zone 110 in the cross-process direction CP. The UV light from the UV curing device 116 hardens the excipient material on the uppermost layer of chemical delivery device 300 to form a durable portion of the chemical delivery device 300. The UV curing process solidifies the excipient material to accept additional layers of excipient material and to form arrays of cavities that can contain a liquid chemical carrier with an active chemical as ejected from the ejectors in one or more printhead arrays, such as the arrays 104A-104C and 108A-108C.

As use herein, the term "leveler" refers to a member that is configured to engage the uppermost surface of each layer of the excipient material in a chemical delivery device before the UV curing device 116 cures the excipient material. In the printer 100, the leveler 118, which is also referred to as a planarizer, applies pressure and optionally heat to smooth the uppermost layer of excipient material in the chemical delivery device 300 and form a uniform surface that receives an additional layer of the excipient material during a subsequent pass through the print zone 110. In some embodiments, the leveler 118 is a roller coated with a low surface energy material to prevent adhesion of the excipient material in the chemical delivery device 300 to the surface of the leveler 118. While the other components in the print zone 110 remain at a predetermined distance in the Z direction from the chemical delivery device 300, the leveler 118 engages the chemical delivery device 300 during at least some passes through the print zone 110 to smooth the uppermost layer of excipient material.

The controller 128 is a digital logic device such as a microprocessor, microcontroller, field programmable gate array (FPGA), application specific integrated circuit (ASIC) or any other digital logic that is configured to operate the printer 100. In the printer 100, the controller 128 is operatively connected to one or more actuators that control the movement of the support member 102, the printhead arrays including the printhead arrays 104A-104C, 108A-108C, and 112A-112C, the UV curing device 116, and the leveler 118. The controller 128 is also operatively connected to a memory 132. In the embodiment of the printer 100, the memory 132 includes volatile data storage devices such as random access memory (RAM) devices and non-volatile data storage devices such as solid-state data storage devices, magnetic disks, optical disks, or any other suitable data storage devices. The memory 132 stores programmed instructions 136 for the operation of the controller 128 to operate components in the printer 100. The memory 132 also stores chemical delivery device structure data 138 that include a three-dimensional (3D) representation of the shape and structure of one or more types of chemical delivery devices including specific arrangements of cavities within the chemical delivery devices. The chemical delivery device structural data 138 include, for example, a plurality of two-dimensional image data patterns that correspond to each layer of excipient material that the printer 100 forms to produce the chemical delivery device 300. The memory 132 also stores concentration parameters 140 that specify the concentration levels of at least one active chemical within one or more regions of the chemical delivery device 300. The memory 132 also stores one or more stochastic or vector halftone screens 142. As described in more detail below, the stochastic or vector halftone screens enable the printer 100 to control the distribution of active chemicals to different portions of the cavities formed in the chemical delivery device 300. The controller 128 executes the stored program instructions 136 to operate the components in the printer 100 to form the three-dimensional structure of the excipient material in the chemical delivery device 300. The controller 128 also executes the stored program instructions to generate halftoned image data and control ejection of drops of the active chemicals into portions of the cavities formed in the chemical delivery device 300 based on the concentration parameter data 140 and halftone screens 142 for different regions of the chemical delivery device 300.

Figure 2:
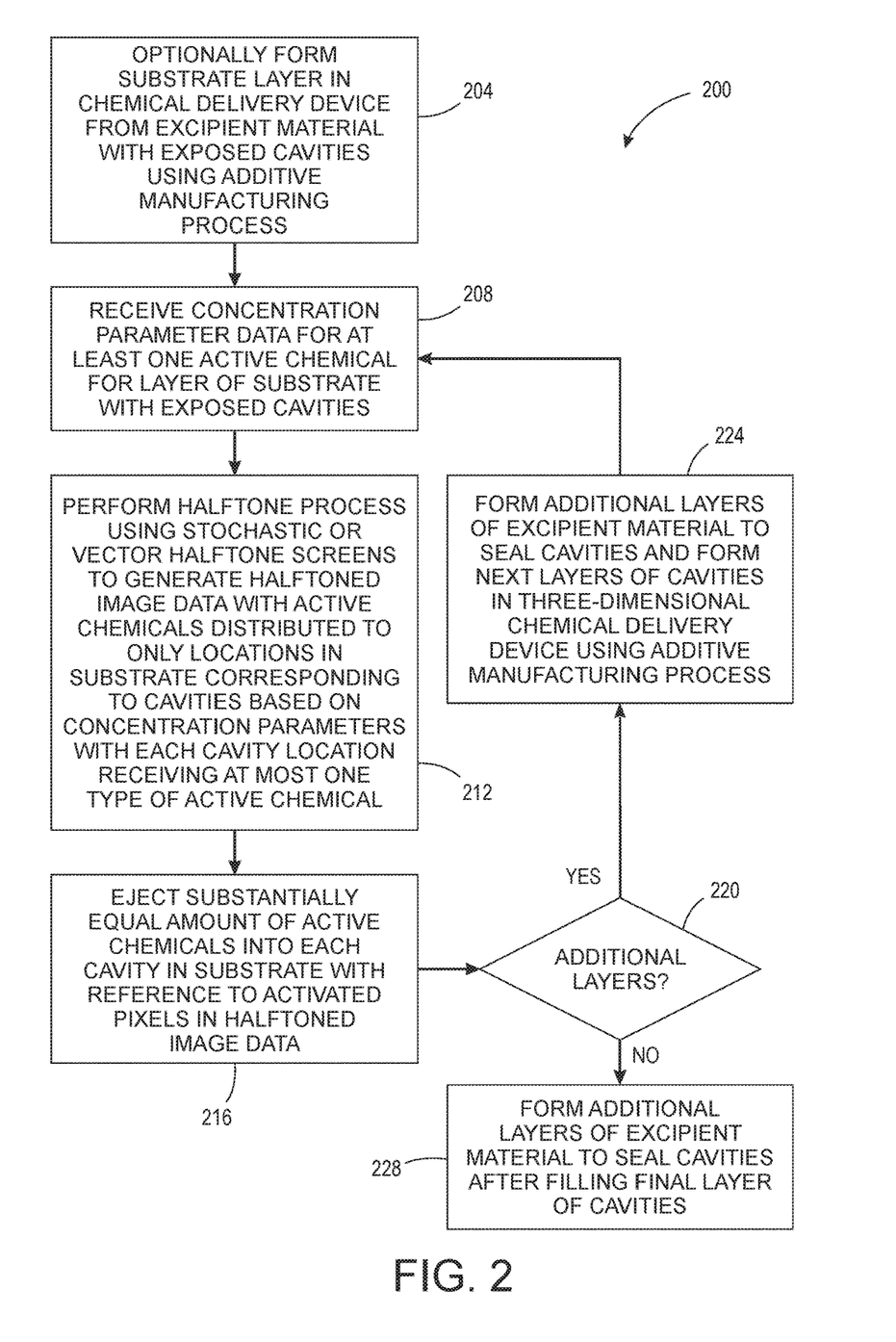
FIG. 2 is a block diagram of a process for forming a chemical delivery device.

FIG. 2 depicts a process 200 for forming a chemical delivery device with a range of concentration levels for one or more active chemicals in a substrate formed with one or more forms of excipient material. In the discussion below, a reference to the process 200 performing an action or function refers to the operation of a controller in an additive manufacturing device, such as a three-dimensional object printer, to execute stored program instructions to perform the function or action in association with components in the additive manufacturing device. The process 200 is described in conjunction with the three-dimensional object printer of FIG. 1 for illustrative purposes.

During process 200, the printer 100 optionally forms a substrate layer in the chemical delivery device from an excipient material with a plurality of exposed cavities that are available to receive an active chemical from the printer 100 during the process 200 (block 204). In one embodiment, the printer 100 forms the substrate from a powdered excipient material using a spreader that supplements the printheads 112A-112C. The controller 128 operates ejectors in one group of the printheads, such as the printheads 112A-112C, to eject a binder material in a predetermined pattern to form a hardened layer of the excipient material. The controller 128 operates the ejectors in the printheads 112A-112C based on the chemical delivery device structure data 138 to form each layer of the chemical delivery device 300 with a predetermined structure and arrangement of cavities. The controller 128 also forms cavities in the substrate in locations that do not receive the binder material where excess powder that does not receive the binder is removed after the printer 100 forms a layer of cavities. The printer 100 generally forms each set of cavities from a plurality of layers of the excipient material that form the floor and lateral walls of each cavity.

In another embodiment, one or more printhead arrays in the printer 100 eject drops of the excipient material that harden to form the substrate and the cavities from multiple layers of the excipient material using, for example, a UV curable polymer or other suitable excipient material. The controller 128 uses the chemical delivery device structure data 138 to control the ejection of drops of the excipient material from the printheads 112A-112C to form layers of the chemical delivery device with the predetermined shape and arrangement of cavities. In still another embodiment, a device other than the printer 100 forms the substrate and the cavities. The printer 100 receives the substrate with exposed cavities on the support member 102.

Figure 3A:
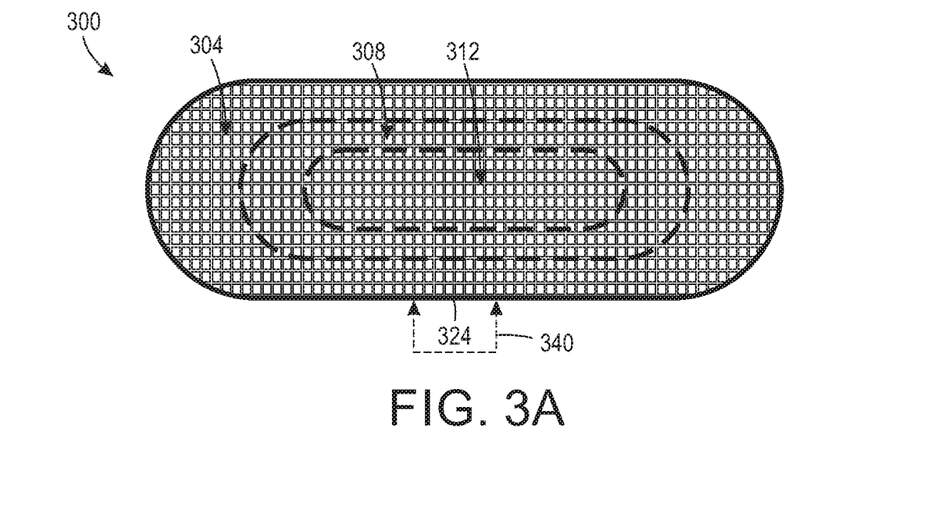
FIG. 3A is a plan view of cavities formed in one layer of a chemical delivery device where each cavity can receive an active chemical.
Figure 3B:
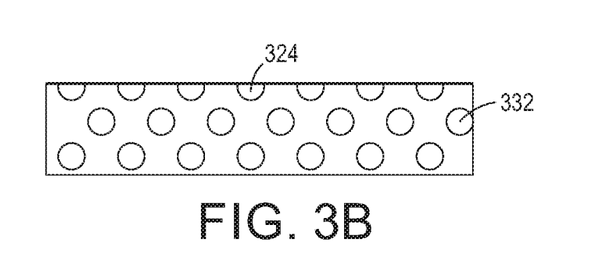
FIG. 3B is a first cross-sectional view of the chemical delivery device of FIG. 3A.
Figure 3C:
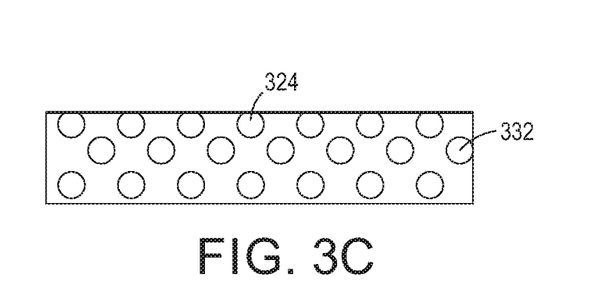
FIG. 3C is a second cross-sectional view of the chemical delivery device of FIG. 3A.

FIG. 3A-FIG. 3C depict an example of a chemical delivery device 300 with multiple layers of cavities. FIG. 3A depicts a plan view of the substrate in the chemical delivery device 300 with an array of cavities, such as cavity 324, formed in one layer of the chemical delivery device 300. In the example of FIG. 3 the printer 100 is configured to generate halftoned image data for an active chemical that is ejected into a portion of the cavities that are shown in FIG. 3A. In the illustrative embodiment of FIG. 3A, the printer 100 receives different concentration parameters for three different regions 304, 308, and 312 in the exposed layer. While FIG. 3A depicts the regions 304-312 in one layer of the chemical delivery device 300, in many embodiments the regions extend through the cavities that are formed in multiple layers of the chemical delivery device 300 to form three-dimensional regions. Furthermore, while FIG. 3A depicts three regions 304-312 for illustrative purposes, alternative configurations can include a different number of regions and further include a gradient of varying concentration parameters throughout the chemical delivery device 300.

FIG. 3B and FIG. 3C depict cross-sectional views of a portion of the chemical delivery device 300 taken along line 340. FIG. 3B depicts one layer of exposed cavities including the cavity 324 where the exposed cavities are approximately hemispherical in shape to receive drops of a liquid chemical carrier and the active chemical. The chemical delivery device includes multiple layers of cavities in a three-dimensional arrangement including the cavity 332. FIG. 3C depicts another configuration in which the excipient material that forms the upper layer, including the cavity 324, by almost completely forming it with an opening at the top of each exposed cavity that is large enough to enable the chemical carrier and active chemical to enter the cavities and to substantially fill the cavities. The excipient material in the chemical delivery device 300 seals the lower layers of cavities. In some embodiments, the printer 100 moves the support member 102 and chemical delivery device 300 through the print zone 110 multiple times to form the structure of the chemical delivery device 300 from the excipient material that provides a structure with multiple layers of cavities. The printer 100 ejects drops of the active chemical to fill a selected portion of the exposed cavities in each layer of the chemical delivery device 300. The operation of the printer 100 to generate halftoned image data for different regions of the chemical delivery device 300 and eject a chemical carrier including one or more active chemicals into different sets of cavities using a stochastic halftone screen or a vector halftone screen is presented in further detail below.

The excipient material that forms the structure of the chemical delivery device 300 isolates each of the cavities from each other to prevent fluid communication between cavities. In particular, the excipient material prevents the formation of fluid channels between cavities that could enable a larger than expected release of active chemical when the excipient material dissolves to expose fluidly coupled cavities. Additionally, in chemical delivery devices that include two or more active chemicals, the isolated cavities prevent the active chemicals from combining prior to the dissolution of the excipient material in the chemical delivery device 300. While FIG. 3B and FIG. 3C depict spherical cavities, the chemical delivery device 300 can include cavities with different sizes and shapes, including oblate spheroids and cylindrical cavities for different types of chemical delivery devices.

As depicted in FIG. 3A, the chemical delivery device 300 includes multiple regions 304-312, and the printer 100 processes concentration parameter data in multiple regions of the substrate to generate halftoned image data that enable delivery of different densities of the active chemicals to the cavities within each region. For example, in one chemical delivery device configuration, the concentration parameters increase from the outermost region 304 through the intermediate region 308 to the innermost region 312. Since the volume of each of the regions decreases from the exterior region 304 to the center region 312, a proper selection of concentration levels enables the chemical delivery device 300 to emit the active chemical at a substantially constant rate as the chemical delivery device 300 dissolves. Of course, in alternative configurations the concentration parameters can affect the rate of emission for the active chemical in a wide variety of ways including a gradient that enables the chemical delivery device 300 to emit one or more active chemicals at varying rates over time as the chemical delivery device 300 dissolves.

While the chemical delivery device 300 is formed with a cylindrical center with two hemispheres at each end of the cylinder in a shape that is often associated with medication tablets and other chemical tablets, the printer 100 is configured to form the substrate with a wide variety of shapes and sizes of the chemical delivery device and individual cavities. The chemical delivery device 300 is merely an illustrative embodiment of a three-dimensional device with a plurality of layers having cavities to receive various concentrations of an active chemical.

Referring again to FIG. 2, the process 200 continues as the printer 100 receives concentration parameter data that specify the concentrations levels for one or more active chemicals in one or more regions of the chemical delivery device (block 208). The concentration parameters include a numeric value that specifies a proportion of the cavities in a given region of the chemical delivery device that receive the corresponding active chemical. In the printer 100, the controller 128 receives stored concentration parameter data 140 from the memory 132. The concentration parameters correspond to one or more active chemicals within at least one region of the chemical delivery device 300. In one embodiment, a concentration parameter for each active chemical is specified as a percentage in a range of 0% to 100% where 0% indicates that the active chemical is absent from a particular region of the chemical delivery device, 100% indicates that all available cavities in the region should receive the active chemical, and an intermediate percentage that corresponds to a specific number of cavities in the region that receive the chemical in the region. Some chemical delivery devices include regions with concentration parameters for two or more active chemicals. The sum of the concentration parameters does not exceed 100% or some other predetermined maximum parameter value to ensure that the substrate has sufficient cavity locations for all of the active chemicals in the region of the chemical delivery device.

Figure 4:
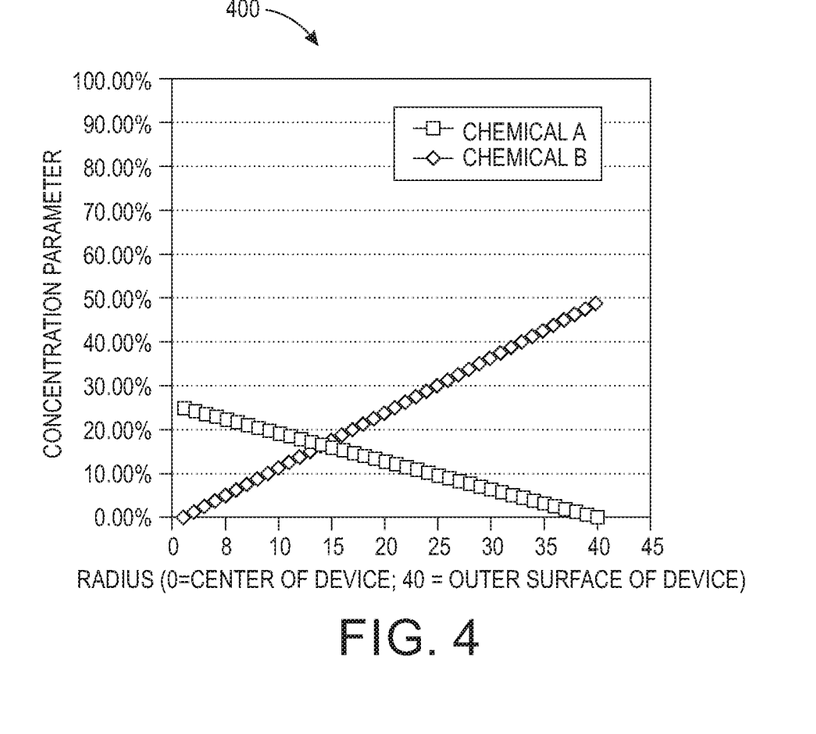
FIG. 4 is a depiction of concentration graphs for halftoned image data corresponding to a distribution of an active chemical within a chemical delivery device.

FIG. 4 depicts a graph 400 of concentration parameters for two different active chemicals (Chemical A and Chemical B) in different regions of a chemical delivery device. In FIG. 4 a total of forty regions in a three-dimensional cylindrical volume approximates the shape of a chemical delivery device, such as the device 300 of FIG. 3. Each region corresponds to a three-dimensional concentric shell starting from a region that surrounds the center of the cylinder (x-index 1) and extending to the exterior of the cylinder (x-index 40). The example of FIG. 4 depicts concentration gradients for the two different active chemicals. As used herein, the term "concentration gradient" refers to a change in the concentration levels of the active chemical distributed through the different regions of the chemical delivery device that the printer 100 produces based on a plurality of concentration parameters for multiple regions in the chemical delivery device. The different concentration gradients enable different configurations of the chemical delivery device to emit the active chemicals at substantially constant rates, increasing or decreasing rates, or even oscillating rates as the chemical device dissolves.

In the example of FIG. 4, the concentration gradient for the first active chemical A specifies a decreasing concentration from the center of the chemical delivery device outwards towards the exterior of the device, while the concentration gradient for the second active chemical B specifies an increasing concentration gradient from the center of the chemical delivery device outwards towards the exterior of the device. Alternative concentration gradients include a plurality of concentration parameters that form non-linear and non-monotonic changes in the concentration through different regions of the chemical delivery device. While FIG. 4 depicts concentration gradients over three-dimensional regions in a chemical delivery device with an approximately cylindrical shape, similar concentration gradients are also applicable to chemical delivery devices with a wide range of shapes. Another approximation of the chemical delivery device 300 of FIG. 3A models the volume of the chemical delivery as a cylinder with two spheres: $V=(4\pi r^2+2\pi rh)\delta r$. Similar approximations for the three-dimensional geometry of various chemical delivery devices are known to those of ordinary skill in the art.

Referring again to FIG. 2, the process 200 continues as the controller 128 in the printer 100 generates halftoned image data using a stochastic halftone screen, (which may also be a vector halftone screen if multiple compounds are being printed) with reference to the one or more concentration parameters in each region of the image data corresponding to the substrate (block 212). The controller 128 generates pixels of image data using the threshold values of corresponding dots in the halftone screens and the threshold ranges of the active chemicals and excipient materials based on the concentration parameters for one or more active chemicals. As used herein, the term "activated pixel" refers to a pixel location in the halftoned image data that receives an active chemical, while the remaining pixels that form the structure of the chemical delivery device receive an inactive or excipient material. In embodiments of the process 200 that form chemical delivery devices with two or more active chemicals, the controller 128 uses the vector halftone screen to generate image data with only one active chemical in any given pixel location of the image data. The printer 100 also ejects drops of excipient material for the remaining pixels that are not activated pixels as is described in more detail below. The halftoned image data include a plurality of activated pixels that correspond only to locations of a portion of a plurality of cavities formed in a substrate that receive an active chemical. In some configurations, a region receives one active chemical while in other configurations a single region receives two or more active chemicals. As described above, the stochastic vector halftone screen includes an arrangement of dots with threshold values that produces halftoned image data with a distribution of pixels that corresponds to the physical arrangement of cavities in the chemical delivery device.

The halftone process generates the halftoned image data with a predetermined arrangement of pixels that corresponds to the locations of cavities that are exposed in the substrate of the chemical delivery device. If the chemicals being dispensed do not have the same dissolution rate as the excipient material in the target solvent, or if multiple chemicals are included which must not touch, then the halftone screen also includes "guard" dots with a predetermined threshold value or range of values that surround the dots corresponding to different cavities in the chemical delivery device. The guard dots have a fixed value that never corresponds to an active chemical. The printer 100 generates the halftoned image data based on the guard dots that includes corresponding "guard" pixels that surround the locations of the cavities and that correspond to the locations of walls and other structures in the substrate that do not receive drops of the active chemicals. In FIG. 5 the halftone screen includes an arrangement of guard dots that correspond to the arrangements of cavities in one layer of the chemical delivery device 300. The guard dots are assigned a predetermined value or range of values (e.g., 255 in the example of FIG. 5) which ensures that they are only used for printing the excipient material, and not any of the active chemicals.

To produce the halftone screens, the controller 128 either uses the predetermined halftone screen data that are stored in the halftone screen data 142 of the memory 132, or the controller 128 generates pseudo-random numeric threshold values for each dot that corresponds to a cavity and that is a candidate to receive an active chemical. Except for situations where a region of the chemical delivery device is saturated to 100% concentration, only a portion of the cavities in each region receives an active chemical. The remaining cavities remain empty or the printer 100 fills the empty cavities with either the excipient material that forms the chemical delivery device 300 or an inactive material, such as water, glycerin, triglycerides, or another liquid. The fill material depends upon the chemical properties of the environment in which the chemical device dissolves. In some embodiments, the chemical carrier that holds the active chemicals in solution also serves as an inactive liquid when ejectors in the printer eject the chemical carrier without any dissolved active chemical. The controller 128 uses a thresholding process described below to identify the portions of the pixels that receive different active chemicals based on the halftone screen dot values and the threshold ranges.

Figure 5:
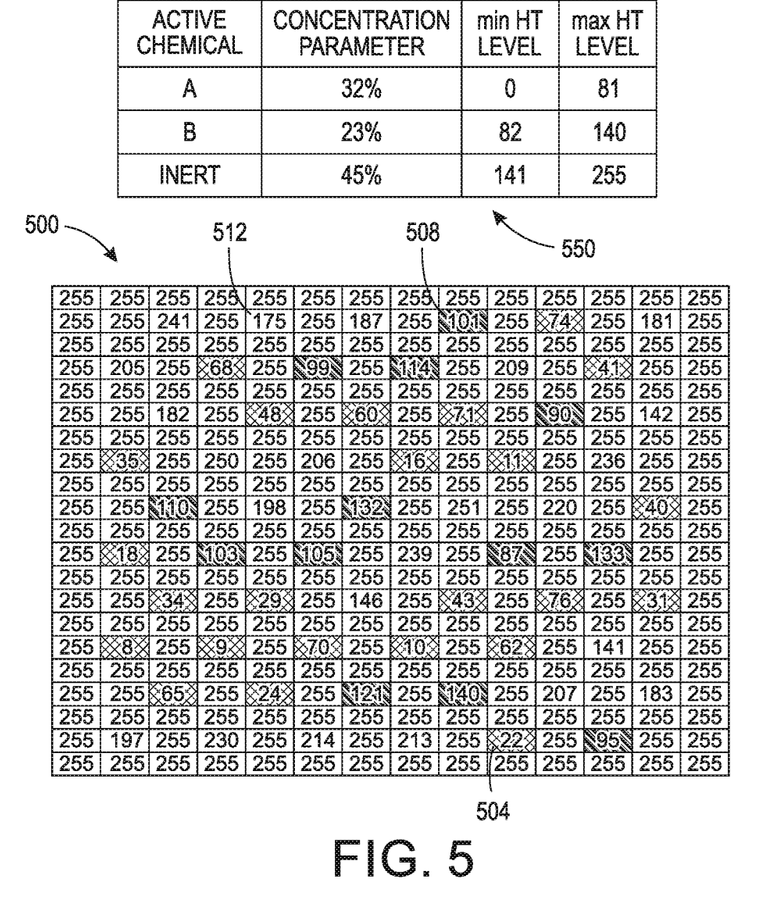
FIG. 5 is a graph depicting a sample of a halftone screen and a corresponding arrangement of image data for two different active chemicals in a region of a substrate of a chemical delivery device.

FIG. 5 depicts a two-dimensional halftone screen 500 corresponding to a single layer of one region of a chemical delivery device that the printer 100 uses during the process 200. The halftone screen 500 is an illustrative example of a stochastic vector halftone screen that is suitable for use in production of a chemical delivery device that incorporates one or more active chemicals. In the printer 100 the memory 132 stores the halftone screen 500 and optionally additional two-dimensional or three-dimensional halftone screens with the halftone screen data 142. FIG. 5 also depicts a table 550 showing the concentration parameters for two different active chemicals that are distributed in the halftoned image data. The halftoned screen data 500 are encoded in an 8-bit numeric range where each dot takes on a value of 0 to 255, although other embodiments use different ranges and the guard dots could be assigned a different value, such as 0, in an alternative configuration. In FIG. 5, the dots with values 255 are each guard dots that correspond to locations of walls or features other than cavities in the substrate of the chemical delivery device, and the printer 100 does not eject drops of active chemicals into the locations corresponding to guard dots. FIG. 5 depicts a single set of guard dots around each potential location for the active chemicals, but alternative embodiments use a different number of guard dots based on the sizes and arrangements of the cavities in the substrate. Some embodiments omit guard dots if separation of the active chemical locations is not required for a particular chemical delivery device. Additionally, while the halftone screen 500 depicts a single dot for each cavity, different halftone screen embodiments include dot arrangements for different sizes and shapes of cavities.

While FIG. 5 depicts the two-dimensional halftone screen 500 that corresponds to a region of a single layer of a larger three-dimensional chemical delivery device, in the printer 100 the halftone screen data 142 typically includes three-dimensional halftone screens that include multiple layers to define a three-dimensional region of the chemical delivery device over multiple layers. Some layers of the halftone screen may include only guard dots that correspond to the excipient material to enable the printer 100 to form protective layers of the excipient material over previously filled cavities in the chemical delivery device. In a three-dimensional halftone screen embodiment, the halftone screen 500 represents one layer in the multi-layer halftone screen. During operation, the printer 100 forms each layer of the chemical delivery device using one selected two-dimensional halftone screen portion of a larger three-dimensional halftone screen for each layer.

In one embodiment, the halftone screen is stored in the memory 132 prior to the printing process. As described below, the printer tiles a single halftone screen in a repetitive process to cover the three-dimensional region occupied by the chemical delivery device for a wide range of chemical device shapes and sizes to enable a comparatively small halftone screen to be used to form the image data in one or more regions of a larger chemical delivery device. The controller 128 adjusts the threshold ranges that receive active chemicals based on the concentration parameter data to enable the printer 100 to use a single halftone screen to produce image data and printed chemical delivery devices with different chemical concentration gradients for one or more active chemicals in different regions of the chemical delivery device. In another embodiment, the controller 128 generates the halftone screen threshold values during the printing process. The controller 128 generates the numeric values in the dot centers of the screen in a pseudo-random manner to produce a more uniform distribution than would be achieved using completely random numbers. For example using a pseudo-random process the controller 128 generates threshold values for the dots where the probability of adjacent cavities having similar halftone levels, which increases the likelihood that adjacent cavities receive the same active chemical, is less than would be expected from a purely random process. In embodiments that use guard dots, the controller 128 only uses the pseudo-random process to produce the threshold values for the dot centers that align with cavities in the chemical delivery device and the guard dots (e.g. dot values of 255 in FIG. 5) remain with fixed values.

During the process 200, the controller 128 generates activated pixels for one or more active chemicals in the portions of the halftoned image data based on the concentration parameters for each active chemical within a region and based on the threshold values in the halftone screen that are assigned to the dot locations for each cavity within the region. As depicted in the table 550 the concentration parameter for a first active chemical (Chemical A) is 32%, and the controller 128 generates a threshold range of 0-81 (e.g. approximately 32% of 256 available values) using the predetermined scale of 0-255 of FIG. 5. Thus, the controller generates activated pixels in halftoned image data that are assigned to the first active chemical corresponding to the locations of dots in the halftoned screen 500 that have a numeric value of 0-81. Table 550 includes another concentration parameter of 23% for the second active chemical (Chemical B) and the controller 128 generates a second numeric range of 82-140 (e.g. approximately 23% of the 256 values with an offset of +82 to avoid overlap with the threshold range of the first chemical) for the second active chemical. The numeric ranges for the first active chemical and the second active chemical are "stacked" meaning that the numeric ranges do not overlap to ensure that the controller 128 selects at most one active chemical for any of the candidate dots in the halftone screen (e.g., dots that do not have the guard value 255) in the image data 500. The remaining dots that correspond to the cavities in the substrate with numeric dot threshold values of 141 to 255 do not receive either of the first or second active chemicals and the controller 128 classifies these pixels as "inactive" in FIG. 5, which indicates that the excipient material or another inactive material should fill cavities that do not receive the active chemicals.

For example, the halftone screen data 500 contains a dot 504 with numeric threshold value 22. The controller 128 generates an activated pixel for the first active chemical in the halftoned image data based on the threshold value and the threshold range for the first active chemical based on the concentration parameter. Similarly, the controller 128 generates an activated pixel for the second active chemical corresponding to the dot 508, which has the numeric threshold value 101. The controller 128 does not generate an activated pixel corresponding to the dot 512 with numeric value 175 since the dot 512 does not fall within the threshold of either active chemical. Instead, the controller 128 generates a pixel that is assigned to the excipient material or another inactive material to fill the cavity that does not receive an active chemical. Similarly, the controller generates image data pixels corresponding to the excipient material for all of the guard dots with the value 255.

In a multi-layer chemical delivery device, the printer 100 optionally generates or uses a pre-defined three-dimensional halftone screen corresponding to the three-dimensional arrangements of cavities in multiple layers of the chemical delivery device. The three-dimensional halftone screen includes dot locations that are candidates to receive active material and guard dots in a similar configuration to the two-dimensional arrangement of dots shown in FIG. 5. Three-dimensional halftone screens include multiple planes of dots similar to the planar screen 500 of FIG. 5 that correspond to different layers of cavities in the chemical delivery device. If the three-dimensional halftone screen is smaller than the object to be printed, the controller 128 tiles multiple copies of the halftone screen, using a space-filling tiling process to produce a larger screen that completely encompasses the three-dimensional volume of the chemical delivery device. During operation, the printer 100 ejects drops of the active chemical or chemicals for an individual layer with a two-dimensional arrangement of cavities with openings that are exposed to the printheads, such as printheads 104A-104C and 108A-108C in the printer 100. Thus, while the printer 100 generates three-dimensional halftoned image data in some embodiments, the printer 100 ejects the active materials into individual layers of cavities in the chemical delivery device that are each arranged in a two-dimensional layer.

In an alternative embodiment, the controller 128 further divides the regions in the three-dimensional chemical delivery device into a series of two-dimensional regions corresponding to each layer of cavities formed in the chemical delivery device. The controller 128 generates or loads from memory, 132, the halftone screen as a two-dimensional arrangement of dots for each layer of cavities in the chemical delivery device based on the concentration parameters and gradients through the two-dimensional layer. Either embodiment of the process 200 enables the printer 100 to form chemical delivery devices with varying distributions of one or more active chemicals.

Referring again to FIG. 2, the process 200 continues as the printer operates at least one ejector to eject a predetermined amount of the active chemical into each cavity in the portion of cavities in the substrate that corresponds to one of the activated pixels with reference to the halftoned image data (block 216). Using the printer 100 as an example, the controller 128 operates the ejectors in the printhead array 104A-104C to fill each cavity in a first portion of cavities that corresponds to the locations of the activated pixels for the first active chemical in the halftoned image data. The ejectors in the printheads 104A-104C eject a predetermined amount of the chemical carrier and the first active chemical into each cavity that corresponds to an activated pixel in the image data to ensure that each region of the chemical delivery device has a concentration of the active chemical that corresponds to the concentration parameter. In the printer 100, the controller 128 operates the ejectors in the printheads 108A-108C to eject the predetermined amount of the chemical carrier including the second active chemical into the second portion of cavities that correspond to the activated pixels for the second active chemical in a similar manner to the operation of the printheads 104A-104C. Using FIG. 3A and FIG. 5 as examples, each of the activated pixels in the image data that the controller 128 generates using the halftone screen 500 aligns with one cavity in the exposed layer of cavities in one region, such as the region 304, of the chemical delivery device 300. The ejectors in the printheads 104A-104C and 108A-108C eject a predetermined amount of the chemical carrier and active chemicals into the cavities that correspond to the first and second active chemicals, respectively, to form each region of the layer in the chemical delivery device 300 with the appropriate concentrations of the active chemicals.

Process 200 continues as described above for any additional layers in the chemical delivery device (block 220). The printer 100 applies additional layers of the excipient material to seal the exposed cavities in the chemical delivery device and encapsulate the active chemicals in any cavities that received the active chemicals, and forms another layer of cavities from the excipient material based on the chemical delivery device structural data 138 to form another layer of cavities in the chemical delivery device (block 224). In the illustrative embodiment of FIG. 2, the controller 128 repeats the processing described in conjunction with blocks 208-216 for an embodiment of the process 200 that generates the activated pixels in the halftoned image data for each layer of the chemical delivery device individually. In another configuration, the process 200 repeats block 216 using previously generated halftone data, such as another two-dimensional arrangement of the halftoned data in a larger set of three-dimensional halftoned data, to control the ejection of the active chemicals into the cavities of the next layer of the chemical delivery device. Process 200 concludes when no additional layers of cavities in the chemical delivery device remain (block 220) and the printer 100 seals the final layer of cavities with the excipient material (block 228).

The printer 100 and process 200 enable additive manufacturing production of chemical delivery devices that release one or more active chemicals at varying rates and that incorporate multiple types of active chemical material with chemical isolation between the active chemicals until the chemical delivery device dissolves. The systems and methods described herein enable production of chemical delivery devices with different shapes and sizes with minimal reconfiguration of the three-dimensional object printer 100. Additionally, the printer 100 can produce chemical delivery devices with different operating characteristics merely by using a different set of concentration parameters to adjust the distribution of active chemicals throughout the structure of the chemical delivery device, or by using an alternate halftone screen.

It will be appreciated that variants of the above-disclosed and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

What is claimed:

1. A three-dimensional object printer comprising:
a support member;
at least a first ejector configured to eject a first chemical carrier including a first active chemical toward the support member; and
a controller operatively connected to the at least first ejector and a memory, the controller being configured to:
receive a first concentration parameter for a first active chemical in a first region of a substrate in a chemical delivery device positioned on the support member;
generate halftoned image data using a stochastic halftone screen stored in the memory and with reference to the first concentration parameter, the halftoned image data including a plurality of activated pixels that correspond only to locations of a first portion of a plurality of cavities formed in a substrate that receive the first active chemical; and
operate the at least first ejector to eject a predetermined amount of a first chemical carrier including the first active chemical into each cavity in the first portion of the cavities in the substrate with reference to the halftoned image data to produce the chemical delivery device with a concentration of the first active chemical corresponding to the first concentration parameter.

2. The printer of claim 1 further comprising:
a dispenser configured to emit an excipient material to form the substrate of the chemical delivery device; and
the controller being operatively connected to the dispenser and further configured to:
operate the dispenser to form the substrate from a plurality of layers of the excipient material on the support member prior to the ejection of the predetermined volume of the first chemical carrier including the first active chemical.

3. The printer of claim 2 the dispenser further comprising:
a spreader configured to emit a powdered excipient material toward the support member; and
at least a second ejector configured to eject a liquid binder in a predetermined pattern to bind portions of the excipient material to form the substrate.

4. The printer of claim 1 the dispenser further comprising:
at least a second ejector configured to eject liquid drops of the excipient material toward the support member in a predetermined pattern to form the substrate.

5. The printer of claim 1, the controller being further configured to:
receive a plurality of concentration parameters of the first active chemical for a plurality of regions of the chemical delivery device;
generate the halftoned image data for the plurality of regions of the chemical delivery device using the stochastic halftone screen stored in the memory with reference to the plurality of concentration parameters; and
operate the at least first ejector to eject the predetermined amount of the first chemical carrier including the first active chemical into the first portion of the cavities in the substrate with a concentration gradient through the plurality of regions of the chemical delivery device corresponding to the plurality of concentration parameters.

6. The printer of claim 1, further comprising:
at least a second ejector configured to eject a second chemical carrier including a second active chemical toward the support member; and
the controller being operatively connected to the at least second ejector and further configured to:
receive a second concentration parameter for a second active chemical in the first region of the substrate in the chemical delivery device;
generate the halftoned image data using the stochastic halftone screen stored in the memory with reference to the second concentration parameter, the halftoned image data including a second plurality of activated pixels that correspond only to locations of a second portion of the plurality of cavities formed in the substrate that receive the second active chemical, wherein the stochastic halftone screen further comprises a stochastic vector halftone screen; and
operate the at least second ejector to eject a predetermined amount of a second chemical carrier including the second active chemical into each cavity in the second portion of the cavities in the substrate with reference to the halftoned image data to produce the chemical delivery device with a concentration of the second active chemical corresponding to the second concentration parameter.

7. The printer of claim 6, the controller being further configured to:
generate the second plurality of activated pixels only in locations of the halftoned image data corresponding to cavities in the substrate that do not correspond to any of the first plurality of activated pixels.

8. The printer of claim 1 further comprising:
a dispenser configured to emit an excipient material toward the substrate of the chemical delivery device; and
the controller being operatively connected to the dispenser and further configured to:

operate the dispenser to form excipient material in any cavity in the plurality of cavities that does not receive the first chemical carrier including the first active chemical.

9. The printer of claim 1 further comprising:
a dispenser configured to emit an excipient material toward the substrate of the chemical delivery device; and
the controller being operatively connected to the dispenser and further configured to:
operate the dispenser to form a plurality of layers of an excipient material over the substrate and the plurality of cavities to cover the plurality of cavities and to form another plurality of cavities in another layer of the substrate of the chemical delivery device after the ejection of the predetermined volume of the chemical carrier including the first active chemical.

10. The printer of claim 1, the controller being further configured to:
generate three-dimensional halftoned image data corresponding to a three-dimensional arrangement of cavities in a plurality of layers of the substrate with reference to the first concentration parameter; and
operate the at least first ejector to eject the predetermined amount of the first chemical carrier including the first active chemical into each of the first portion of the cavities with reference to a two-dimensional arrangement in the three-dimensional halftoned image data corresponding to the plurality of cavities formed in one layer of the substrate.

* * * * *